United States Patent [19]

Brenman et al.

[11] Patent Number: 4,637,405
[45] Date of Patent: Jan. 20, 1987

[54] APPARATUS FOR STIMULATING SALIVATION

[75] Inventors: Henry S. Brenman, Cinnaminson; Philip Katz, Princeton Junction, both of N.J.; Graydon E. Beatty, Philadelphia, Pa.

[73] Assignee: Biosonics, Inc., Philadelphia, Pa.

[21] Appl. No.: 661,667

[22] Filed: Oct. 17, 1984

Related U.S. Application Data

[62] Division of Ser. No. 481,331, Apr. 1, 1983, Pat. No. 4,519,400.

[51] Int. Cl.⁴ .............................................. A61N 1/36
[52] U.S. Cl. .................................... 128/787; 128/421
[58] Field of Search ...................... 128/741, 642, 82.1, 128/783, 787, 802, 419 R, 421–423; 604/20

[56] References Cited

U.S. PATENT DOCUMENTS

| 527,037 | 10/1894 | Funk | 128/787 X |
| 3,277,892 | 10/1966 | Tepper | 128/787 X |
| 4,244,373 | 1/1981 | Nachman | 128/787 X |
| 4,334,542 | 6/1982 | Takinishi et al. | 128/642 |

Primary Examiner—Lee S. Cohen
Attorney, Agent, or Firm—Robert C. Podwil

[57] ABSTRACT

A stimulator for inducing salivation by neural stimulation comprises a housing which may be received in the oral cavity of a user, the housing enclosing electronic signal generating means and electrodes for applying a signal to neurally sensitive areas of the oral cavity to induce salivation. In its method aspect, the invention involves stimulation of salivation by the application of an electrical signal to neurally sensitive areas.

12 Claims, 11 Drawing Figures

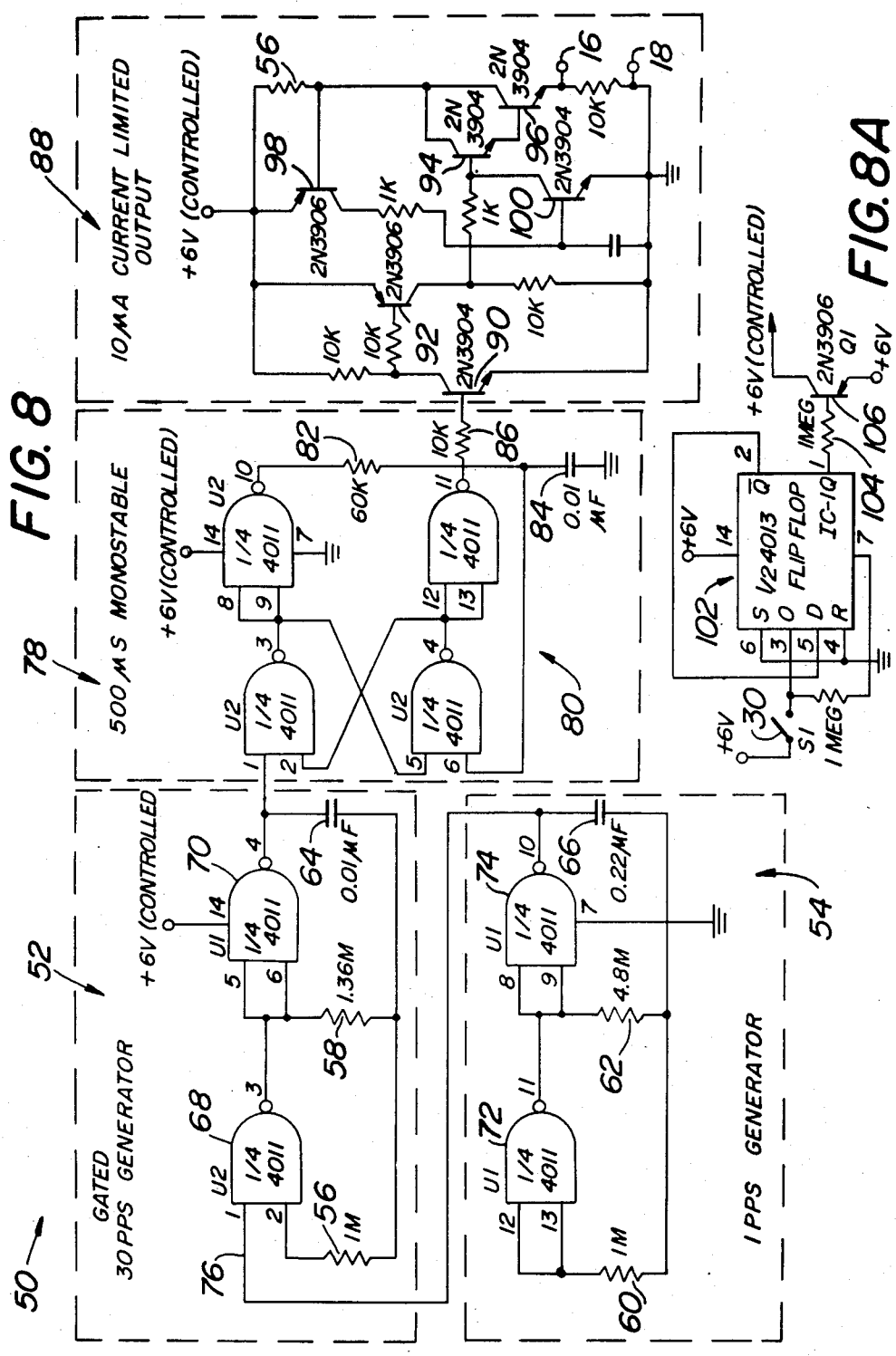

APPARATUS FOR STIMULATING SALIVATION

This application is a division of application Ser. No. 481,331, filed Apr. 1, 1983, now U.S. Pat. No. 4,519,400.

BACKGROUND OF THE INVENTION

This invention relates to apparatus and a method for stimulating salivation, and more particularly, to apparatus and a method for stimulating salivation by the application of electrical energy to nerves in the region of the oral cavity. Such stimulation, it has been found, can produce salivation by reflex action, by creating parasympathetic outflow to the salivary glands, parotid, submaxillary or sublingual.

When a patient is subjected to radiation treatment for carcinoma of the oral pharyngeal region, the radiation often produces as a side effect injury which results in the eventual necrosis of the salivary glands or the nerves associated with them. The injury may be unilateral or bilateral, depending upon the site of the application of the radiation and the dosage delivered. Loss of salivation results in drying of the epithelium of the oral cavity, attended by persistent and often debilitating pain and other symptoms.

The salivary glands can be stimulated to flow by electrically stimulating three nerve groups within the oral cavity and the surrounding region. These are: the maxillary nerve with its three divisions (anterior, middle and posterior), the mandibular nerve with its divisions and the lingual nerve. In general, the nerves of interest in connection with this invention have components which, when stimulated, produce reflex stimulation of the salivary glands.

The principal object of this invention is to provide a small, simple and effective apparatus to create an electrical stimulus which is capable of inducing salivation.

Another object of this invention is to provide a method for inducing salivation by means of electrical stimulation.

Other objects will appear hereinafter.

It has heretofore been proposed that electrical energy be applied in the oral cavity for a variety of medical reasons, but not for the purpose nor in the manner described herein. For example, in Russian Pat. No. 721,109, issued Aug. 15, 1977, a method is disclosed for treating inflammation of salivary glands by filling the salivary ducts with a liquid medication under pressure, and then using the liquid to carry out electrophoresis.

In German Offenlegungschrift No. 2740-188, published Mar. 8, 1979, a technique is disclosed for the application of an electrical stimulus to the gums to prevent, so the publication states, atrophy or bleeding of the gums and decay of the teeth.

In addition, it has heretofore been proposed (1) that electricity be applied to teeth or dental work to test neural response, (2) that electricity be applied to the gums to induce absorption of medicine by the gums, and (3) that pyorrhea be treated by the application of electricity. The above concepts, however, are not pertinent to the problem addressed by the present invention, or to its solution.

The above and other objects of this invention are realized, in a presently preferred form of the apparatus, by a stimulator which comprises a housing small enough to be comfortably received within the oral cavity of a user, the housing having an enclosure within which is housed a microcircuit and power supply capable of generating an electrical signal and a control switch. Associated with the housing, and electrically connected to the signal generator, are active and ground electrodes which apply the electrical signal to an area of the oral cavity which is determined by investigation to be neurally sensitive. Identification of the neurally sensitive area may be accomplished by applying to the oral cavity, on an exploratory basis, an electrical signal which simulates the salivation-inducting signal produced by the signal generator. One presently preferred technique for accomplishing this is the use of glove-mounted electrodes of the kind described in U.S. application Ser. No. 06/452,319, filed Dec. 22, 1982, now U.S. Pat. No. 4,510,939 for "MEANS FOR TRANSFERRING ELECTRICAL ENERGY TO AND FROM LIVING TISSUE" (assigned to the Assignee of the present application). It has been found that the application of a stimulus in the above manner induces salivation in those patients in whom pathosis is not so advanced or so profound that they cannot be helped by the present apparatus and method. In other words, if a patient has nerve function sufficient to increase salivation in response to the evaluative or diagnostic stimulus, that patient may be considered a logical candidate for the present apparatus and method. If a nerve has been so irradiated that it proves incapable of transmitting an impulse, then the glove and its associated electrode are placed in the region of the next potentially efficacious nerve. Thus, if the first-evaluated nerve was the maxillary, the next might be the mandibular nerve or, in turn, the lingual nerve on the tongue, until salivation is produced. If in fact salivation is not produced by stimulation on one side of the face (or medial plane), stimulus may be applied to the other side of the face until salivation is produced. Evaluation in this manner identifies a neurally sensitive "target", an area to which a stimulator in accordance with this invention may apply a stimulating signal.

In accordance with the present invention, therefore, at least one active electrode is juxtaposed as closely as possible to an area identified as neurally sensitive to electrical stimulation, and the stimulator may be maintained in place by a dental appliance clipped to the teeth or by association with a denture.

In its method aspect, the present invention involves the technique of identifying one or more neurally sensitive areas within the oral cavity; positioning with respect to those areas at least one active electrode capable to applying to those areas a stimulating signal; and generating a stimulating signal and applying the signal to sensitive area.

There are seen in the drawings forms of the invention which are presently preferred (and which represent the best mode contemplated for carrying th invention into effect), but it should be understood that the invention is not limited to the precise arrangements an instrumentalities shown or described.

DESCRIPTION OF DRAWINGS

FIGS. 8, 8A and 9 are schematic circuit diagrams illustrating exemplary electronic circuit means for use in the present invention.

DETAILED DESCRIPTION

Figure 1:
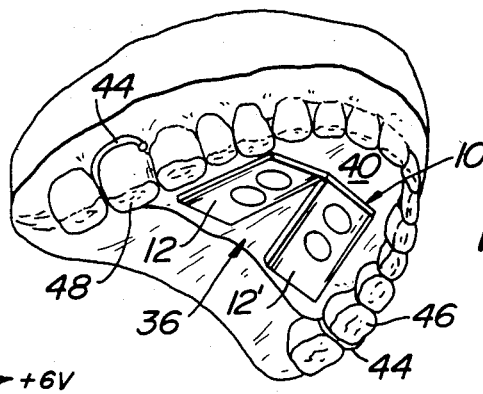
FIG. 1 is a perspective view, showing one embodiment of apparatus in accordance with the invention, operatively disposed with respect to the teeth and hard palate of a user.

Referring now to the drawings in detail, wherein like reference numerals indicate like elements, there is seen in FIGS. 1 through 7, apparatus, designated generally by the reference numeral 10, for inducing salivation by neural stimulation.

The apparatus 10 comprises a two-section housing 12, 12', adapted, as is perhaps best seen in FIGS. 1 through 3, 6 and 7, to be received within the oral cavity of a user.

Disposed on an outer surface 14 of the housing 12 are electrodes, such as the active electrode 16 and ground or passive electrode 18 in the illustrated embodiment. As is perhaps best seen in FIGS. 1, 3, 6 and 7, the electrodes 16 and 18 are located in the area of the hard palate of a user, juxtaposed to the tongue (which does not itself appear in the drawings).

Figure 4:
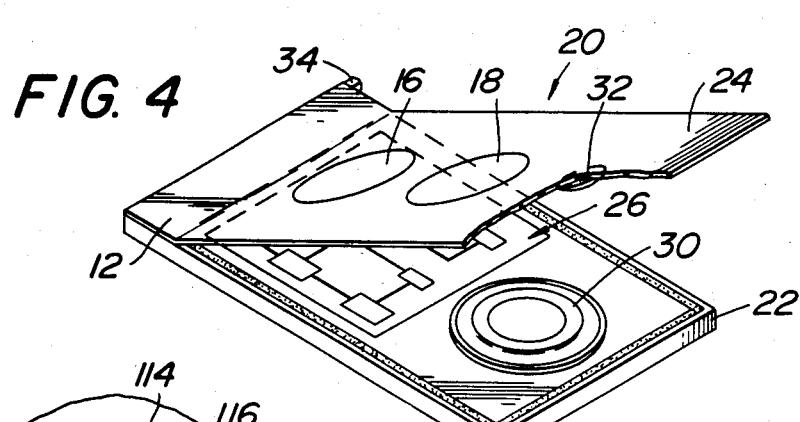
FIG. 4 is a perspective view of a housing and associated components of an apparatus in accordance with the invention.

Referring now to FIG. 4, the housing section 12 provides an enclosure, designated generally by the reference numeral 20, defined by a rigid tray-like member 22 and a somewhat flexible cover member 24. When the housing 12, 12' is disposed for operation, the enclosure 20 is sealed, and is liquid and gas-impervious. The member 22 and cover member 24 may be made from numerous well-known chemically inert plastic polymeric materials suitable for use in the body. As is seen in FIG. 4, housed within the enclosure 20 are electrical and electronic components and circuitry, designated generally by the reference numeral 26. In general, the electrical and electronic circuitry includes a highly miniaturized and self-contained signal generator with associated control circuitry. The housing section 12', which is constructed in a manner similar to the housing section 12, houses a power supply, designated generally by the reference number 28, and carries additional active and passive electrodes 16', 18'. Associated with the housing 12, 12' and signal generator 26, is a tongue-actuable switch 30.

Referring now to FIG. 4, it will be seen that the cover member 24 is, in the illustrated and presently preferred form of the invention, a flexible membrane, and that the switch 30 is a normally open switch disposed beneath the cover member 24. The switch 30 may be of the pressure-actuated type commonly used in "membrane" type keyboards for hand-held calculators, microcomputers and the like. Switches which are functionally equivalent to "Type BM" switches, from SP America, Inc., are suitable. The application of tongue pressure to the cover member 24 in the area of the switch 30 is thus capable of closing the switch, to effect operation of the apparatus 10 in the manner described below. A projection 32 may be provided on the underside of the cover member 24, to facilitate the transmission of pressure to the switch 30.

Referring to FIGS. 1 through 3 and 5 through 7, the power supply 28, in the presently preferred form of the invention, the power supply comprises a pair of 3.0 volt lithium batteries (Sanyo lithium cells or equivalent), connected in series to produce 6 volts. The power supply 28 in the housing section 12' is electrically connected to the circuitry 26 within the housing 12 by an insulated conductor 34, and both housing sections 12, 12' are affixed, as is seen in FIGS. 1 through 3, 6 and 7, to either an appliance 36 (seen in FIGS. 1 through 3) or a denture 38 (seen in FIGS. 6 and 7). Adhesive or other suitable fastening means may be used to affix the housing sections 12, 12' to the appliance 36. Consistently with the principles of this invention, the housing sections may also be fashioned integrally with the appliance 36.

Figure 2:
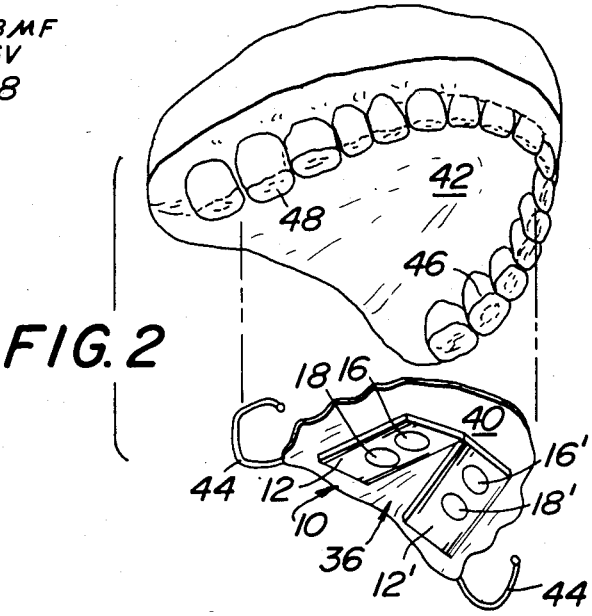
FIG. 2 is a view similar to FIG. 1, showing the apparatus separated from the palate and teeth of the user.
Figure 3:
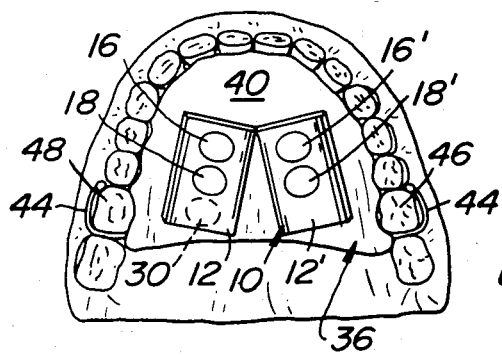
FIG. 3 is a plan view of an apparatus of the type shown in FIGS. 1 and 2.

Referring now to FIGS. 1 through 3, the appliance 36 consists of a plate 40, molded from an impression of the hard palate 42 of the user. Associated with the plate 40 are clips 44 which serve to affix the plate 40 to teeth of the user, such as the molars 46 and 48. Frictional engagement of a fore part of the plate 40 with the front teeth of the user, in association with the clips 44, serves to hold the appliance 36 in place.

Figure 6:
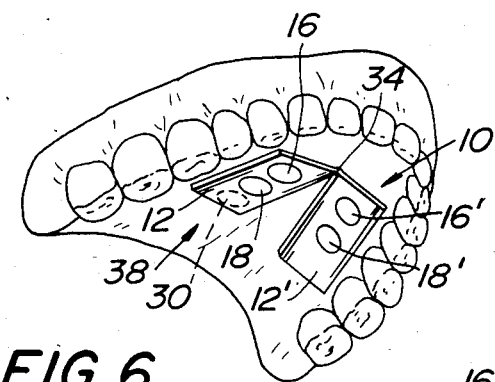
FIG. 6 is a perspective view, similar in its vantage point to FIGS. 1 and 2, but showing apparatus in accordance with the invention associated with a denture.
Figure 7:
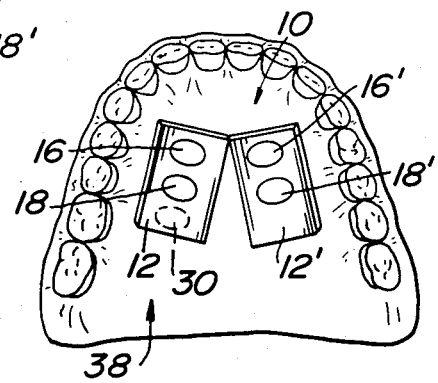
FIG. 7 is a view similar to FIG. 3, but showing apparatus in accordance with the invention associated with a denture.

In FIGS. 6 and 7, the apparatus 10 is shown in association with an upper denture 38. The apparatus 10, it will be seen, is in this instance affixed by any convenient means to a portion of the denture corresponding to the position of the hard palate. Thus, just as in the case of the above-described embodiment in which the apparatus 10 is associated with an appliance 36, the tongue of the user may operate a switch 30 to activate the electrodes 16 and 16'.

FIG. 8 illustrates presently preferred electronic circuitry, designated generally by the reference numeral 50, by which stimulating signals can be produced. Other specific circuitry capable of performing the same function may occur to those skilled in the art. It should be understood that the electronic circuitry 50 uses commercially available components, and because the apparatus 10 is intended for use within the oral cavity (making size an important consideration), the presently desired configuration of the device utilizes microminiature components in the "SO₂", "LIDS" or "DICE" size packages, although any standard CMOS equivalent integrated circuitry (chips) can be used to fabricate the circuitry 50.

The circuitry 50 is designed to produce an output of approximately 12 mA which is calculated on the basis of an assumed output voltage of 4 volts into an impedance of 330 ohms, and it will produce a constant output voltage regardless of the impedance fluctuations across the mucosa of the user. Such fluctuations are and can be expected to be considerable due to the fact that the medium surrounding the electrodes 16 and 18 may be very dry before salivation is induced and very wet afterwards, with large impedance changes between the two conditions. A current limited configuration, as is presently preferred, avoids high current spikes which might occur in low impedance conditions, and conserves battery power.

Referring again to the electronic circuitry 50, the first stage of the circuitry 50 comprises an astable multivibrator, consisting of the above-mentioned function generators 52 and 54 and capacitors 64 and 66 in their respective feedback loops. The function generator 52 is a 30 pulses per second generator, made up of two-quarters of a CD 4011 equivalent (quad 2-input NAND) integrated circuit 68 and 70. The integrated circuits 68 and 70, as well as the integrated circuits 72 and 74 associated with the function generator 54, are of a type sold by Amperex Electronics Corporation, a subsidiary of North American Phillips Corp., as so-called leadless inverted devices ("LIDS"), and are electronically equivalent, however, to large-sized integrated circuits. In other words, the integrated circuits 68, 70, 72 and 74 are LIDS equivalents to the CMOS 4011 integrated circuits available from numerous manufacturers, including, among others, RCA, Texas Instruments Corp., National Semiconductor and Solid State Scientific. The values of passive components 56, 58 and 64 of the function generator 52 are so selected that the output frequency of that stage is 30 pulses per second. The function generator 52, however, is itself turned on and off, that is, gated, by a one pulse per second input, at 76, from the one pulse per second generator 54. Thus, the function generators 52 and 54 produce a constant voltage output of 30 pulses per second, turned on and off at half-second intervals by the one pulse per second output of the function generator 54. The output of this function generator is applied to a stage which consists of a monostable multivibrator, designated generally by the reference numeral 78. The monostable multivibrator stage 78 comprises a commercially available CD 4011 equivalent integrated circuit, designated generally by the reference numeral 80, associated with passive components such as resistor 82, capacitor 84 and output resistor 86. The integrated circuit 80 and its passive components provide a monostable amplifier which sets the pulse width of the signal at a desired 500 microseconds.

The output of the monostable multivibrator stage 78 drives a stage 88 which provides a constant voltage output with an output current limitation of approximately 12 mA. In the stage 88, the output of the stage 78 drives a transistor stage 90, which in turn drives a transistor stage 92 and then a Darlington pair consisting of the transistors 94 and 96. The Darlington configuration provides a current gain squared function. Transistor stages 98 and 100 provide negative feedback to the Darlington pair 94, 96 to reduce the output voltage and thereby prevent the output current from exceeding 12 mA. The action of the transitor stages 98 and 100 also protects the output from accidental shortcircuiting. Transistor stages 92 and 98 of the Amperex LDA 452 type, LIDS equivalents to 2N3906 transistors. Transistor stage 90 and the paired transistors 94 and 96 are Amperex LDA-404 or equivalent, LIDS equivalents to 2N3904 transistors.

Referring now to FIG. 8A, there is seen an arrangement for enabling stimulation, using the tongue-actuable switch 30 to control pulse output, and hence stimulation.

The switch 30 controls a flip-flop, designated generally by the reference numeral 102, which performs a latching function with respect to the power supply of the circuitry 50. The flip-flop 102 in its presently preferred form, is based upon a LIDS equivalent 4013 integrated circuit (LFF 4013), supplying, through the output resistor 104 a transistor 106 (Amperex LDA 452, LIDS equivalent to 2N3906). Changing the state of the flip-flop 102 by momentary actuation of the switch 30 will turn on the six volt supply to the circuitry, thus enabling stimulation. The circuitry illustrated in FIG. 8A provides, therefore, both a latching function (enabling continuous stimulation) and a controlled six volt power supply for the circuitry 30.

Figure 9:
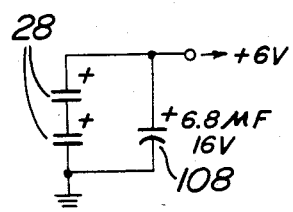

FIG. 9 illustrates schematically a power supply arrangement suitable for use in the invention, in which two batteries 28 (Sanyo lithium CR 1220, 3 v.) are connected in series, and associated with a capacitor 108. The batteries 28 provide an uncontrolled six volt (6 v.) source for the circuitry.

Figure 10:
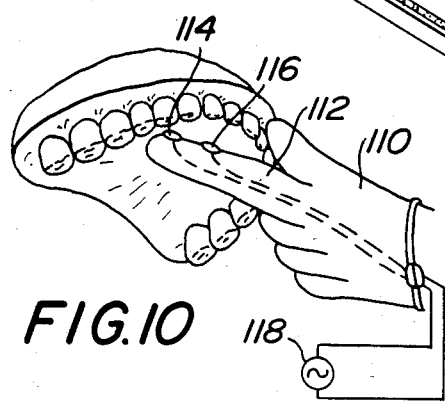
FIG. 10 illustrates the manner in which neural stimulation may be used to locate neurally sensitive areas for the purpose of this invention.
Figure 5:
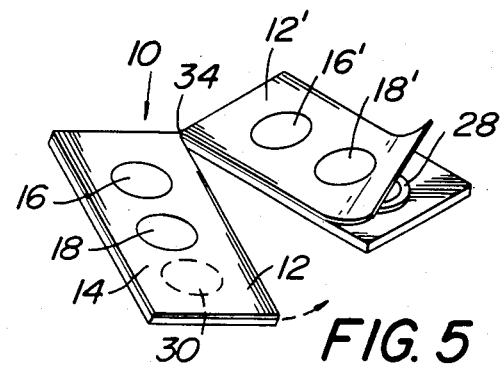
FIG. 5 is a perspective view showing the apparatus prior to positioning on a dental appliance or denture.

FIG. 10 illustrates, somewhat schematically, the above-described technique for identifying neurally sensitive areas, to which the active electrodes 16 of the apparatus 10 may advantageously be juxtaposed.

Referring to FIG. 10, a surgical glove 110 of the kind described in greater detail in the above-mentioned U.S. application Ser. No. 06/452,319, has on its first finger 112 a pair of electrodes 114 and 116. In this instance, the electrodes 114 and 116 are preferably approximately one-quarter inch in diameter, and approximtely one-half to three-eights inch apart on the palmar surface of the first finger 112. The electrodes 114 and 116 are electrically connected to a source 118 of electrical energy, specifically, the output of a signal generating circuit 118 analogous to the above-described electronic circuitry 50. Thus, the signal generating circuit 118 can apply across the electrodes 114 and 116 of the glove 110 a potentially nerve-stimulating signal similar to the signal produced by the actual apparatus 10. The signal generating circuit, it has been found, may be contained in a small module or housing, not shown, clipped to the cuff of the glove 110 or otherwise associated with it.

In using the above technique in the preferred manner, a clinician first places the electrodes 114 and 116 in the area of the maxillary buccinator, that is the fornix of the palate, first to one side of the mid-line and then to the other. Increased salivation will be observed when the electrodes contact a neurally sensitive area if the patient has in that area nerve function capable of transmitting the impulse.

As is indicated above, if the first-tried nerve provides an unsatisfactory response, others may be tried, and eventually a location suitable for the apparatus 10 may be found.

In the illustrated forms of the apparatus 10, the electrodes 16 and 18 face downwardly and are positioned to contact the tongue. In some instances, however, it will be advantageous to position the electrodes in juxtaposition to the palate, so as to stimulate the nerves of that region. In such an application, the physical arrangement of the apparatus 10 would be suitably modified to assure the proper contact and to facilitate access of the tongue of the user to the switch 30, but the principle by which the apparatus stimulates salivation would remain the same.

It should be understood, therefore, that the present invention may be embodied in other specific forms without departing from its spirit or essential attributes. Accordingly, reference should be made to the appended claims, rather than the foregoing specifications, as indicating the scope of the invention.

What we claim is:

1. Apparatus for inducing salivation by neural stimulation at neurally sensitive areas within the oral cavity of a user, comprising a housing adapted to be received within the oral cavity of a user, said housing having an enclosure therein, an electrical signal generator disposed in said enclosure, said signal generator including a power supply, at least one electrode operatively associated with said housing and electrically coupled to said signal generator, said electrode being so positioned with respect to said housing as to be juxtaposed to and in operative contact with a neurally sensitive area of the oral cavity, the stimulation of which by electrical energy can induce salivation, when said housing is operatively disposed, whereby said electrode applies a signal generated by said signal generator to the sensitive area to induce salivation.

2. Apparatus in accordance with claim 1, and means for coupling said housing to the hard palate of the user.

3. Apparatus in accordance with claim 2, and switch means associated with said housing and said signal generator for activating and deactivating said signal generator, said switch means being adapted for operation by the tongue of a user.

4. Apparatus in accordance with claim 2, and a carrier for said housing, said carrier being so configured as to conform closely to the topological configuration of the hard palate of a user, said housing being affixed to said carrier.

5. Apparatus in accordance with claim 4, and said carrier having clip means thereon for removably securing said housing to the teeth of a user.

6. Apparatus in accordance with claim 2, and said housing being affixed to a denture.

7. Apparatus in accordance with claim 1, and a switch associated with said housing and said signal generator for activating said signal generator, said switch being adapted for operation by the tongue of a user.

8. Apparatus in accordance with claim 1 wherein said housing comprises a pair of sections, one of said sections containing said power supply.

9. Apparatus for inducing salivation by neural stimulation at neurally sensitive areas within the oral cavity of a user, comprising a housing adapted to be received within the oral cavity of a user, said housing having an enclosure therein, an electrical signal generator disposed in said enclosure, said signal generator including a power supply, a switch associated with said housing and said signal generator for activating and deactivating said signal generator, said switch being adapted for operation by the tongue of a user, at least one electrode operatively associated with said housing and electrically coupled to said signal generator, said electrode being so positioned with respect to said housing as to be juxtaposed to and in operative contact with a neurally sensitive area of the oral cavity, the stimulation of which by electrical energy induces salivation when said housing is operatively disposed, whereby said electrode applies a signal generated by said signal generator to the sensitive area to induce salivation, said signal generator comprising means for producing a series of pulses having an amplitude of about three to five volts, a pulse width of about 500 micro-seconds and a frequency of about 30 Hz.

10. Apparatus in accordance with claim 9, wherein said signal generator comprises means to turn the signal on and off at intervals of about one-half second.

11. Apparatus in accordance with claim 10, wherein said signal generator comprises a multivibrator and a power amplifier.

12. Apparatus in accordance with claim 9, wherein said signal generator comprises a multivibrator and a power amplifier.

* * * * *